United States Patent
Kim et al.

(10) Patent No.: US 12,173,949 B2
(45) Date of Patent: Dec. 24, 2024

(54) DELIVERY ROBOT LOADING BOX STATE MANAGEMENT SYSTEM AND METHOD THEREFOR

(71) Applicant: WOOWA BROTHERS CO., LTD., Seoul (KR)

(72) Inventors: Myung Sik Kim, Suwon-si (KR); Jin Seok Park, Seoul (KR); Jun Woo Kim, Yongin-si (KR)

(73) Assignee: WOOWA BROTHERS CO., LTD., Seoul (KR)

( * ) Notice: Subject to any disclaimer, the term of this patent is extended or adjusted under 35 U.S.C. 154(b) by 197 days.

(21) Appl. No.: 17/916,009

(22) PCT Filed: Mar. 22, 2021

(86) PCT No.: PCT/KR2021/003509
§ 371 (c)(1),
(2) Date: Sep. 29, 2022

(87) PCT Pub. No.: WO2021/201479
PCT Pub. Date: Oct. 7, 2021

(65) Prior Publication Data
US 2023/0160623 A1    May 25, 2023

(30) Foreign Application Priority Data

Mar. 31, 2020 (KR) .................. 10-2020-0039302
Jul. 21, 2020  (KR) .................. 10-2020-0090130

(51) Int. Cl.
*F25D 11/00*  (2006.01)
*A61L 9/20*   (2006.01)
(Continued)

(52) U.S. Cl.
CPC ............. *F25D 11/003* (2013.01); *A61L 9/20* (2013.01); *B25J 11/008* (2013.01); *F25D 23/02* (2013.01);
(Continued)

(58) Field of Classification Search
CPC .... F25D 11/003; F25D 23/02; F25D 2300/00; F25D 2331/804; F25D 2700/12;
(Continued)

(56) References Cited

U.S. PATENT DOCUMENTS 11,338,430 B2    5/2022  Kato et al.
2019/0353418 A1*  11/2019  Akinci .................. A61L 9/205
2021/0096572 A1    4/2021  Jang et al.

FOREIGN PATENT DOCUMENTS

JP    05-048051    6/1989
KR    20-0288896   9/2002
(Continued)

OTHER PUBLICATIONS

Written Opinion of International Searching Authority dated Jul. 19, 2021 for International Patent Application No. PCT/KR2021/003509.
(Continued)

*Primary Examiner* — Cassey D Bauer
(74) *Attorney, Agent, or Firm* — PnK IP LLC (57) ABSTRACT

A delivery robot loading box state management system includes a loading box provided in a delivery robot such that a delivery product is loaded therein; a sensing unit capable of detecting the state of the inside of the loading box; a
(Continued)

temperature control unit capable of adjusting the temperature inside the loading box; a deodorizing unit for removing odors inside the loading box; and a control unit for controlling the operation of at least one of the temperature control unit or the deodorizing unit according to the detection result of the sensing unit.

6 Claims, 4 Drawing Sheets (51) Int. Cl.
  *B25J 11/00* (2006.01)
  *F25D 23/02* (2006.01)
(52) U.S. Cl.
  CPC ..... *A61L 2209/111* (2013.01); *F25D 2300/00* (2013.01); *F25D 2331/804* (2013.01); *F25D 2700/12* (2013.01)

(58) Field of Classification Search
  CPC ......... F25D 2317/0417; F25D 2400/32; A61L 9/20; A61L 2209/111; B25J 11/008; B25J 11/0045
  See application file for complete search history.

(56) References Cited

FOREIGN PATENT DOCUMENTS

| KR | 10-1929483 | 12/2018 |
| KR | 10-2019-0117417 | 10/2019 |
| WO | 2019049366 | 3/2019 |

OTHER PUBLICATIONS

International Search Report dated Jul. 19, 2021 in International Application No. PCT/KR2021/003509 (with English Translation).

* cited by examiner

Control temperature using heated (or cooled) liquid

FIG. 7

When internal odor is sensed, drive UV lamp and turn off lamp after decomposition of odor molecules

DELIVERY ROBOT LOADING BOX STATE MANAGEMENT SYSTEM AND METHOD THEREFOR

CROSS REFERENCE TO RELATED APPLICATION

This application is a National Stage Entry of International Application No. PCT/KR2021/003509, filed Mar. 22, 2021, which claims priority to and the benefit of Korean Patent Application No. 10-2020-0039302, filed Mar. 31, 2020 and Korean Patent Application No. 10-2020-0090130, filed Jul. 21, 2020, each of which is hereby incorporated by reference for all purposes as if fully set forth herein.

BACKGROUND

Field

Embodiments of the invention relates generally to a delivery robot loading box state management system and method therefor, and more particularly, to a technical idea that enables temperature control and odor removal of a loading box inside a delivery robot during delivery using a delivery robot.

Discussion of the Background

According to a related art, when delivering food, etc., a delivery man uses a delivery bag, or performs delivery as it is packaged in containers and plastics in a store.

Figure 1:
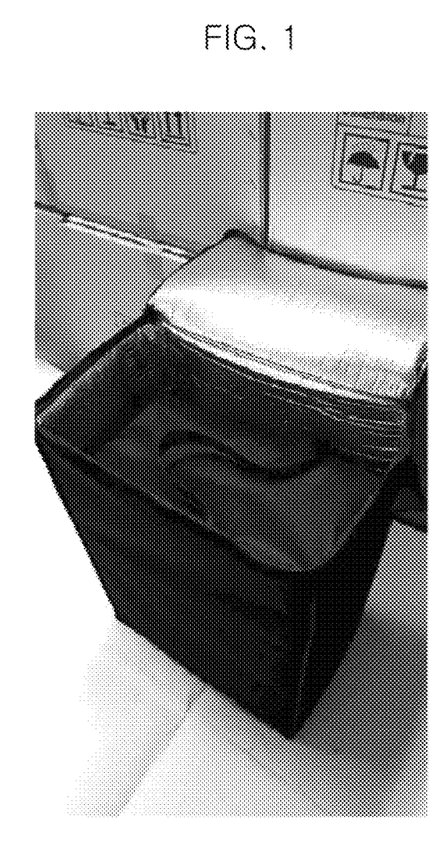
FIG. 1 is a diagram illustrating an example of a delivery bag of a delivery man according to a related art.

FIG. 1 is a diagram illustrating an example of a delivery bag of a delivery man according to the related art.

Referring to FIG. 1, a delivery bag using a thermal insulation material is shown. Such a thermal insulation material may reduce the temperature change of the food loaded inside the delivery bag by suppressing the temperature change inside the delivery bag. For example, it is possible to prevent a decrease in the temperature of hot food or, in case of cold or frozen food, insert a separate ice pack to maintain a low temperature.

In such method according to the related art, it is possible to maintain the temperature at a predetermined level because there is a thermal insulation/cooling material, but when applied to a delivery robot, there is an issue that the load due to the insertion/removal of the ice pack may increase because it is desired to replace the ice pack for cold storage.

In addition, because the temperature control according to the method according to the related art depends on the initial temperature of the food loaded inside the loading box, a temperature change is inevitable as the delivery time passes.

In addition, in the method according to the related art, air is blocked in order to block contact with the outside, and at this time, there is an issue in that the food or packaging material may become wet as moisture is inside.

In addition, there is an issue that the odor of food remains strongly inside the delivery bag or loading box because air entry is blocked, so the odor may be mixed during delivery of the next food which may cause discomfort.

Therefore, rather than relying on the initial temperature of the food inside by simply inserting a thermal insulation/cooling material as in the related art, a technical idea capable of sensing the state of the inside of the loading box and controlling the temperature or removing the odor is desired.

In particular, in a situation where the delivery service using the delivery robot has not been widely used yet, the technical idea that may provide an improved delivery service to customers by controlling the conditions such as the temperature and odor inside the loading box of the delivery robot is lacking.

Therefore, there is a need for a technical idea to improve the quality of the delivery service by the delivery robot by easily managing not only the delivery bag of the delivery man according to the related art, but especially the loading box of the delivery robot, so that the competitiveness of the delivery service using the delivery robot may be reconsidered.

(Patent Document 1) Korean Patent (Registration No. 10-2015994, "Loading Box for Ascon Temperature Lowering Prevention")

The above information disclosed in this Background section is only for understanding of the background of the inventive concepts, and, therefore, it may contain information that does not constitute prior art.

SUMMARY

An aspect provides a technical idea that senses the state inside the loading box of the delivery robot with a sensor to effectively perform temperature maintenance and control, and to easily perform temperature controlling and odor removal of inside.

Additional features of the inventive concepts will be set forth in the description which follows, and in part will be apparent from the description, or may be learned by practice of the inventive concepts.

A delivery robot loading box state management system according to an example embodiment for addressing the technical issues includes a loading box provided in a delivery robot in which a delivery product is loaded, a sensor capable of sensing a state inside the loading box, a temperature controller capable of adjusting a temperature inside the loading box, a deodorizer for removing odors inside the loading box, and a controller for controlling an operation of at least one of the temperature controller or the deodorizer according to a sensing result of the sensor, wherein the controller is configured to control the temperature controller based on a predetermined recommended temperature of the delivery product such that the temperature inside the loading box sensed by the sensor corresponds to the recommended temperature, and drive the deodorizer when an odor sensed by the sensor is greater than or equal to a predetermined concentration.

In addition, the temperature controller may include a cooling and heating device capable of performing functions of a heater and a cooler, or a liquid accommodated in a container capable of heating or cooling, which is loaded in the loading box.

In addition, the deodorizer may include a UV lamp.

In addition, the controller may control opening and closing of a cover of the loading box, and may be configured to open the cover for a predetermined time based on the sensing result of the sensor when the delivery product is loaded in the loading box, or open the cover for a predetermined time when a certain amount of time passes after the delivery product loaded in the loading box is unloaded.

In addition, the delivery robot loading box state management system may further include a fan capable of generating wind from the inside of the loading box to the outside, and the controller may be configured to control the fan to be driven when the cover is opened.

In addition, the controller may be configured to control the temperature controller, when delivery of a first delivery product is completed, to correspond to a recommended temperature of a second delivery product to be delivered before the second delivery product is loaded.

In addition, the controller may be configured to drive the deodorizer before a second delivery product to be delivered is loaded when delivery of a first delivery product is completed.

According to an example embodiment of the inventive concepts, there is an effect that food may be delivered to customers in an optimal condition, by sensing the state inside the loading box with a sensor to effectively perform temperature maintenance and control, and to easily perform temperature controlling and odor removal of inside.

As a result, the quality of the delivered food may be maintained high, which has the effect of improving the competitiveness of the delivery service using the delivery robot.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are illustrated in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As customary in the field, some embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some embodiments may be physically separated into two or more interacting and discrete blocks, units, and/or modules without departing from the scope of the inventive concepts. Further, the blocks, units, and/or modules of some embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Because the inventive concepts may be implemented in various forms and may have various example embodiments, specific example embodiments are illustrated in the drawings and described in detail. However, this is not intended to limit the inventive concepts to specific example embodiments, and should be understood to include all modifications, equivalents, and substitutes included in the spirit and scope of the inventive concepts. In describing the inventive concepts, if it is determined that a detailed description of a related known technology may obscure the gist of the inventive concepts, the detailed description thereof will be omitted.

Terms such as first, second, and the like may be used to explain various components, but the components should not be limited to the terms. The terms are used only to distinguish one component from another component.

Terms used in the present application are only used to describe specific example embodiments, and are not intended to limit the inventive concepts. The singular forms are intended to include the plural forms unless the context dictates otherwise.

The terms such as "comprise" or "have," when used in this specification, are intended to specify the presence of stated features, integers, steps, operations, elements, components, or a combination thereof, but do not preclude the presence or addition of one or more other features, integers, steps, operations, elements, components, and/or groups thereof.

Figure 2:
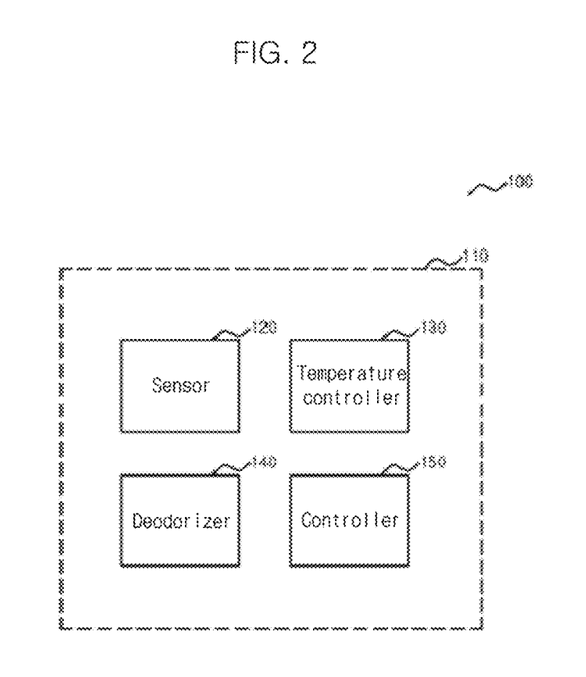
FIG. 2 illustrates a schematic configuration of a delivery robot loading box state management system according to an example embodiment.

FIG. 2 illustrates a schematic configuration of a delivery robot loading box state management system according to an example embodiment.

Referring to FIG. 2, a delivery robot loading box state management system 100 according to an example embodiment may include a loading box 110, a sensor capable of sensing a state inside the loading box 110, a temperature controller 130 capable of adjusting a temperature inside the loading box 110, a deodorizer 140 configured to remove odors inside the loading box 110, and/or a controller 150 configured to control an operation of the temperature controller 130 and/or the deodorizer 140 according to a sensing result of the sensor 120.

The loading box 110 may have a loading space formed therein so that a product to be delivered (e.g., delivery food, etc.) may be loaded.

In the present specification, the case in which the loading box 110 is provided in the delivery robot and delivery of the delivery product is performed by the delivery robot is described as an example, but the present invention is not necessarily limited thereto. For example, it may be easily inferred that the technical idea of the present invention may be applied not only to a delivery robot but also to a separate delivery bag or a delivery box provided by an existing delivery person to deliver a delivery product, to an average expert in the technical field to which the present invention belongs. Hereinafter, for convenience of description, a case in which the loading box 110 is provided in the delivery robot and delivery by the delivery robot is performed will be mainly described.

Further, in the present specification, for convenience of description, the case in which the delivery product is delivery food is described as an example, but the delivery product is not limited to delivery food. Even if the delivery product is not food, the technical idea of the present invention may be applied regardless of the type if it is possible to load in the loading box 110 and it is desired to keep warm/cool in the loading box 110, or if it is desired to manage the odor inside the loading box 110.

The sensor 120 may sense a temperature and/or odor inside the loading box 110. For example, when a predetermined food is loaded in the loading box 110, the temperature sensed immediately after the food is loaded and the temperature sensed as time passes while delivery is performed may vary, and the sensor 120 may sense such temperature change inside the loading box.

In addition, the sensor 120 may sense an odor inside the loading box 110. Here, the sensor 120 may sense the degree of odor (concentration/strength) inside the loading box 110.

To this end, the sensor 120 may include a temperature sensor configured to sense temperature and/or a predetermined olfactory sensor configured to sense odor. Because a sensor capable of sensing temperature or odor molecules in a specific space is widely known, a detailed description thereof will be omitted herein.

Meanwhile, the temperature controller 130 may adjust the temperature inside the loading box 110.

Figure 3:
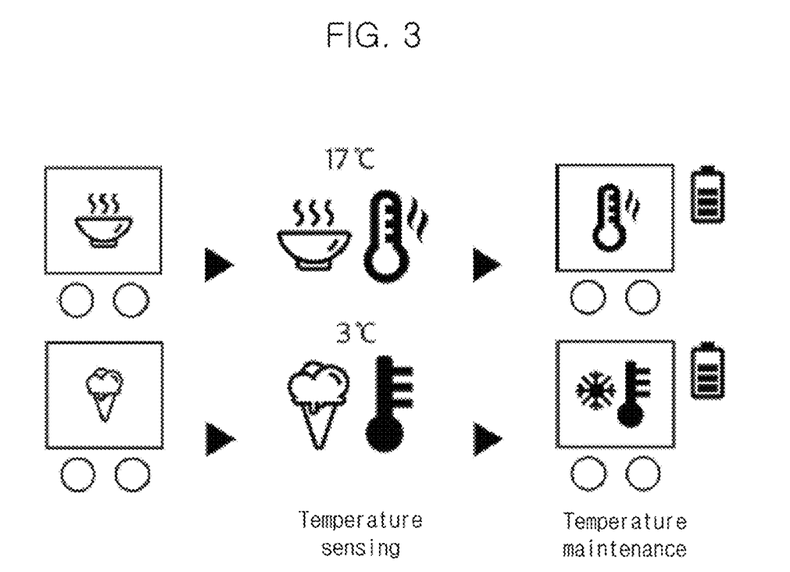
FIG. 3 is a diagram illustrating a temperature control concept of a delivery robot loading box state management system according to an example embodiment.

FIG. 3 is a diagram illustrating a temperature control concept of a delivery robot loading box state management system according to an example embodiment.

The temperature controller 130 may be implemented as a predetermined temperature control device capable of heating or cooling the air inside the loading box 110, such as a heater or a cooler. The temperature control device may use a thermoelectric element capable of heating or cooling through the Peltier effect, or may be implemented as a device such as a heater heated through electric energy or a cooler using a predetermined refrigerant.

Such temperature control may be desired to provide better service to customers, especially when it is desired to maintain a constant temperature during delivery due to the nature of the delivery products (for example, menus that lose flavor when cooled, menus that melt or lose freshness as time passes at room temperature, etc.).

Depending on the example embodiment, the delivery robot loading box state management system 100 may control or maintain the temperature inside the loading box 110 using a predetermined liquid. Such an example is illustrated in FIG. 6.

Figure 6:
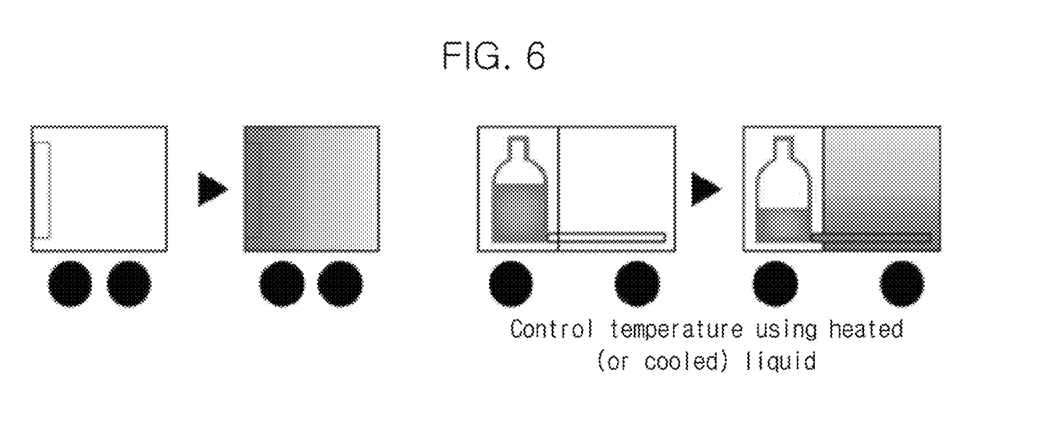
FIG. 6 is a diagram illustrating a specific example of a temperature control method of a delivery robot loading box state management system according to another example embodiment.

FIG. 6 is a diagram illustrating a specific example of a temperature control method of a delivery robot loading box state management system according to another example embodiment.

Referring to FIG. 6, a container 10 accommodating a predetermined liquid may be provided in advance in the loading box 110. The predetermined liquid may be water, and may be a solution in which a predetermined chemical treatment is added or a predetermined chemical substance is added and synthesized as desired. In the present specification, for convenience of description, the liquid is implemented with water, and the water is heated or cooled in the container 10 to be used as hot water or cooling water as an example. The present invention is not necessarily limited thereto.

The hot water or cooling water may be used by heating or cooling the water stored in the container 10 provided in the loading box 110 in advance as desired, and depending on the delivery product to be loaded in the loading box 110, when loading the delivery product, the container 10 containing hot water or cooling water may be selectively loaded together. In the former case, a separate device configured to heat or cool the container 10 may be provided inside the loading box 110. Alternatively, the water inside the container 10 may be heated or cooled by driving the temperature controller 130 without a separate device.

As illustrated in the drawing, the container 10 in which the hot water or cooling water is accommodated may be stored in a space separated from the space in which the delivery product is to be loaded and may be implemented to heat/cool the delivery product and/or the space in which the delivery product is loaded through a predetermined heat transfer means. According to an example embodiment, the container 10 may be implemented to suppress the temperature change of the delivery product by being loaded together with the delivery product in the same space of the inside of the loading box 110.

In this way, when using hot water or cooling water, the temperature inside the loading box 110 may be kept constant within a predetermined level without driving the temperature controller 130 according to the delivery distance (time), and even when the temperature controller 130 is driven, the driving range and driving time may be reduced to have the effect of effectively saving energy.

According to another example embodiment, the temperature controller 130 may control the temperature of the entire inside of the loading box 110, as well as control the temperature of only a portion while heating or cooling a partial range.

For example, a holder capable of holding a container containing a beverage among the delivery products may be provided inside the loading box 110. In this case, the temperature controller 130 may intensively heat or cool only the holder or a limited range near the holder to keep the loaded beverage hot or cold.

As such, the driving of the temperature controller 130 configured to control the internal temperature of the loading box 110 and/or the temperature within a limited range (e.g., a holder, etc.) may be performed by the controller 150.

The controller 150 may perform a function of controlling calculations and other configurations for implementing the technical idea of the inventive concepts. The controller may include a processor, a storage device, and a program stored in the storage device and executed by is the processor. Hereinafter, in the present specification, when the controller 150 performs a predetermined operation, an average expert in the art may easily infer that the processor may be performed by a series of data processing and/or control performed by executing the program.

For example, the controller 150 may control the temperature inside the loading box 110 by driving the temperature controller 130 according to the sensing result of the sensor 120, or control the operation of the deodorizer 140 according to the sensing result.

According to an example embodiment, the controller 150 may control the temperature controller 130 so that the temperature inside the loading box 110 corresponds to a preset temperature. For example, a temperature that may prevent the delivery food loaded in the loading box 110 from cooling during the delivery time may be preset according to the characteristics of the delivery food. Hereinafter, in the present specification, a temperature that is preferable to be maintained according to the characteristics of a delivery product (e.g., delivery food) is referred to as a recommended temperature. Then, when the temperature inside the loading box 110 deviates from a predetermined standard based on the recommended temperature according to the sensing result of the sensor 120, the controller 150 may control the temperature inside the loading box 110 to correspond to the recommended temperature by driving the temperature controller 130.

Information on the characteristics of the delivery product used for such purpose, for example, information such as the type of the delivery product, recommended temperature, etc., may be stored in advance in the controller 150 before delivery is performed by the delivery robot. For example, the information on the characteristics of the delivery product may be input to the controller 150 through order information when the customer places an order, or the controller 150 may extract desired information (e.g., type of delivery product, recommended temperature, etc.) is from the order information. Alternatively, the subject that manages the delivery robot may transmit desired information to the controller 150 through a predetermined management system, or it is also possible to input the information before the delivery robot departs at a store that prepares delivery products and delivers the delivery products through the delivery robot. To this end, the controller 150 may transmit/receive desired information while performing communication with a POS terminal of a store or a system of a management subject that manages the delivery robot loading box state management system 100.

Meanwhile, the controller 150 may control the operation of the deodorizer 140 according to the sensing result of the sensor 120 as described above. To this end, as described above, the sensor 120 may include an olfactory sensor capable of sensing the odor inside the loading box 110.

Figure 4:
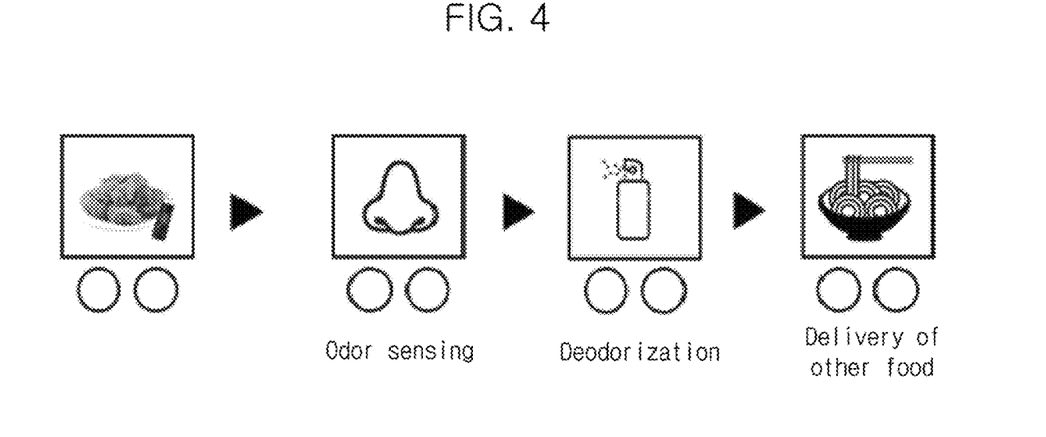
FIG. 4 is a diagram illustrating an odor removal concept of a delivery robot loading box state management system according to an example embodiment.
Figure 7:
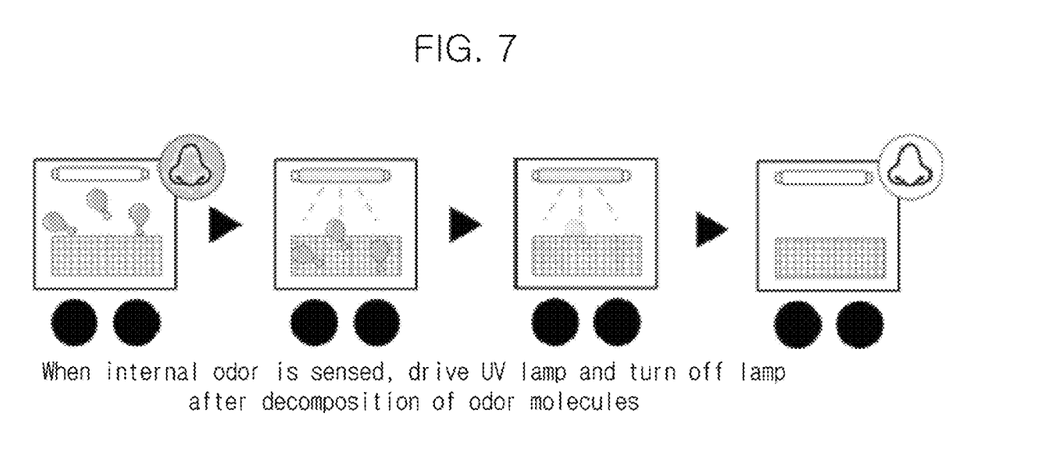
FIG. 7 is a diagram illustrating a specific example of an odor removal method of a delivery robot loading box state management system according to an example embodiment.

FIG. 4 is a diagram illustrating an odor removal concept of a delivery robot loading box state management system according to an example embodiment, and FIG. 7 is a diagram illustrating a specific example of an odor removal method of a delivery robot loading box state management system according to an example embodiment.

According to an example embodiment, when the odor sensed by the sensor 120 exceeds a predetermined concentration, the controller 150 may drive the deodorizer 140 to remove the odor inside the loading box 110.

Alternatively, the controller 150 may remove the odor inside the loading box 110 while repeatedly driving the deodorizer 140 for a predetermined time at regular intervals.

The deodorizer 140 for such purpose may be implemented in various ways.

For example, the deodorizer 140 may include a UV lamp 20 as illustrated in FIG. 7, and the controller 150 may control the driving of the deodorizer 140 while controlling on/off of the UV lamp 20.

Depending on the example embodiment, the deodorizer 140 may be implemented in the form of a deodorizing filter capable of absorbing or filtering odors. In this case, the deodorizer 140 may always perform odor removal even without the control of the controller 150.

According to another example embodiment, the deodorizing filter is covered by a separate case or cover or the like inside the loading box 110, and odor removal may be performed while the controller 150 opens the case or cover.

According to another example embodiment of the inventive concepts, the delivery robot loading box state management system 100 may control the temperature inside the loading box 110 or remove the odor while introducing external air into the loading box 110. Such an example is illustrated in FIG. 5.

Figure 5:
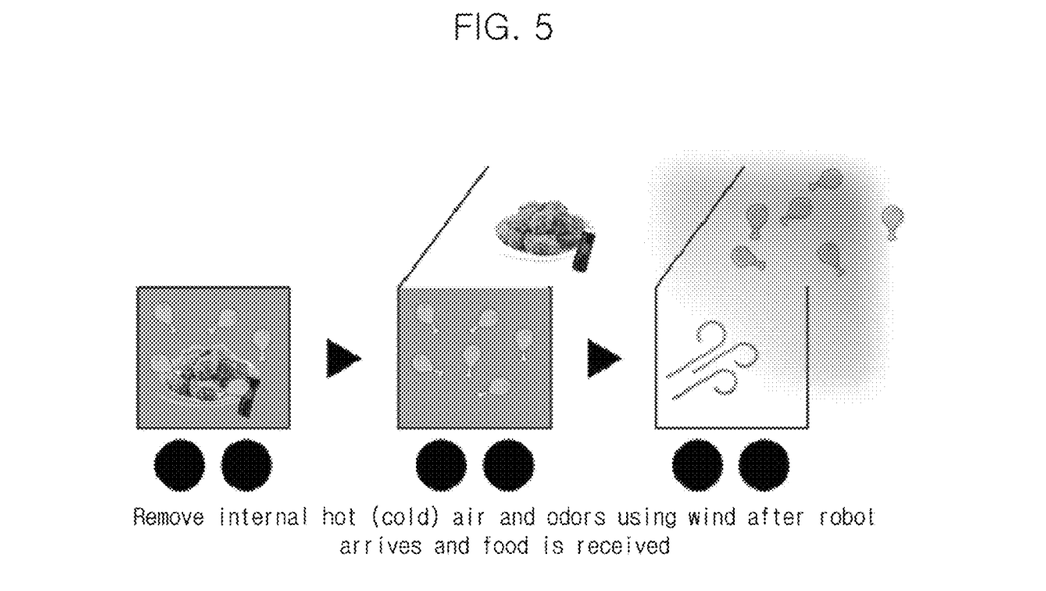
FIG. 5 is a diagram illustrating a method of introducing an outside air of a delivery robot loading box state management system according to an example embodiment.

FIG. 5 is a diagram illustrating a method of introducing an outside air of a delivery robot loading box state management system according to an example embodiment.

Referring to FIG. 5, the controller 150 may control opening and closing of the cover of the loading box 110. For example, the controller 150 may open the cover of the loading box 110 for a predetermined time to introduce outside air into the loading box 110, so that the inside temperature of the loading box 110 is close to room temperature, or to allow internal odors of the loading box 110 to be discharged to the outside.

Here, the delivery robot loading box state management system 100 may include a fan (not illustrated) driven toward the outside inside the loading box 110. When the fan (not illustrated) is driven, the air inside the loading box 110 and the outside air may circulate more smoothly, and the odor inside the loading box 110 may be more easily discharged to the outside. The driving of the fan (not illustrated) may also be controlled by the controller 150.

The opening and closing of the cover of the loading box 110 may be made while the delivery product is loaded in the loading box 110 and delivery is performed, or after the delivery is completed and the delivery product is unloaded from the loading box 110.

In addition, the cover of the loading box 110 may be fully opened within the movable range, but may be opened only by a partial range within the movable range. Such an opening range of the cover may be variable depending on circumstances such as whether the delivery robot is currently running, whether it is stopped, or whether the delivery product is loaded in the loading box 110.

Such an opening and closing of the cover of the loading box 110 may be performed together with the operation of the temperature controller 130 and/or the deodorizer 140.

For example, when an odor of a predetermined concentration or higher is sensed by the sensor 120, the controller 150 may open the cover of the loading box 110 while driving the deodorizer 140 (e.g., driving the UV lamp 20). In addition, the controller 150 may drive a fan (not illustrated) provided in the loading box 110 while opening the cover. In this case, the odor may be effectively removed within a relatively short time. The opening of the cover and driving of the fan (not illustrated) are not necessarily performed together, and even if the cover is opened, the fan (not illustrated) may not be driven as desired.

In addition, if desired, the controller 150 may separately control the operation of the temperature controller 130 and/or the deodorizer 140 or the opening and closing of the cover.

In addition, such operations for temperature control, deodorization, and/or external air inflow by the controller 150 may or may not be selectively performed depending on the characteristics of the first delivery product currently being delivered by the delivery robot and the second delivery product scheduled to be delivered later.

For example, assuming that both the first delivery product and the second delivery product are food, when information on the next delivery food (i.e., information on the second delivery product) is given, if the characteristics of the second delivery product are the same as or similar to those of the first delivery product, the controller 150 may not perform the above-described series of processes. For example, when the next delivery food (second delivery product) is the same menu (e.g., chicken) as the previous food (first delivery product), the controller 150 may not control the temperature or remove the odor inside the loading box 110 where the temperature rises due to the first delivery product and the odor of chicken remains. The controller 150 may always perform the above-described temperature control/deodorization process regardless of the type or characteristics of each of the first delivery product and the second delivery product, and even if temperature control is not performed, desired processes such as deodorization process may be selectively performed.

If, as described above, whenever the cover is opened, a fan (not shown) provided in the loading box 110 is driven to generate wind blowing outward, not only customers who receive the food, but also the staff who load the food, and the delivery man may feel uncomfortable because of the cold/hot air or smelly wind.

Therefore, according to the inventive concepts, after the customer receives the delivery product and leaves, in other words, when it is determined that the delivery is completed because the loading box 110 is emptied, the controller 150 may perform a process of generating wind by driving the fan (not shown) while opening the cover of the loading box 110 again after a certain period of time passes.

On the other hand, there may be cases in which the cover is not arbitrarily opened by the controller 150 except when delivering (or loading) the delivery product because the loading box 110 has a function of automatically closing or locking. In this case, it may be implemented to maintain the open state without closing the cover that opens when the delivery robot arrives at the delivery location and the customer receives food, and after a predetermined time (for example, the time during which the customer who has received the delivery product may move away from the vicinity of the loading box 110 or the time during which the delivery robot moves more than a certain distance from the delivery location) passes, to drive the fan (not shown) to discharge the air inside the loading box 110 to the outside, and close the cover before the delivery robot returns.

Meanwhile, according to another example embodiment of the inventive concepts, the internal temperature control of the loading box 110 may also be performed in a state in which the delivery product is not loaded, for example, in a process of the delivery robot moving (or returning) for the next delivery after the delivery of the delivery product is completed.

For example, when there is information on the next delivery product (e.g., delivery food) as described above, the controller 150 may control the operation of the temperature controller 130 to pre-adjust the internal temperature of the loading box to a temperature suitable for the next delivery product while moving to load the next delivery product.

If there is no next delivery schedule or there is no information about the next delivery product, the controller 150 may adjust the internal temperature of the loading box 110 to correspond to room temperature, or may not perform an operation for temperature control.

Meanwhile, according to another example embodiment of the inventive concepts, it may be implemented to form a hole that may be opened and closed inside the loading box 110 while passing to the outside, so that even if the cover of the loading box 110 is not opened, the internal air is discharged to the outside through the hole.

In addition, according to an example embodiment, the delivery robot loading box state management system 100 may further include a humidity controller (not shown) configured to separately control humidity inside the loading box 110. In this case, the delivery robot loading box state management system 100 may control moisture when the moisture is generated inside the loading box 110 by a specific delivery product such as high-temperature food, thereby preventing the inside of the loading box 110 from getting wet.

The operation of the humidity controller (not shown) may also be controlled by the controller 150. In addition, the humidity controller (not shown) may be implemented as a separate device and provided inside the loading box 110, but the controller 150 may be implemented to control not only the temperature but also the humidity inside the loading box 110 by using driving of the temperature controller 130, opening and closing of the cover, and/or driving of the fan (not shown). In this case, the sensor 120 may further include a hygrometer or a humidity sensor configured to sense humidity.

After all, according to the technical idea of the inventive concepts, because the condition inside the loading box 110 may be adjusted according to the characteristics of the delivery product when delivery is performed by the delivery robot, it is possible to significantly improve the competitiveness of the delivery service using the delivery robot.

The foregoing description of the inventive concepts is for illustration, and those skilled in the art to which the inventive concepts pertains can understand that modifications into other specific forms may be easily made without changing the technical spirit or essential features of the inventive concepts. Therefore, it should be understood that the example embodiments described above are illustrative in all respects and not restrictive. For example, each component described as a single type may be implemented in a distributed manner, and components described as distributed may be implemented in a combined form.

The scope of the inventive concepts is indicated by the appended claims rather than the above detailed description, and all changes or modifications derived from the meaning and scope of the claims and their equivalent concepts should be construed as being included in the scope of the inventive concepts.

The inventive concepts may be used in a delivery robot loading box state management system and a method therefor.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A delivery robot loading box state management system comprising:
    a loading box provided in a delivery robot in which a delivery product is loaded;
    a sensor capable of sensing a state inside the loading box;
    a temperature controller capable of adjusting a temperature inside the loading box;
    a deodorizer for removing odors inside the loading box; and
    a controller for controlling an operation of the temperature controller and the deodorizer according to a sensing result of the sensor,
    wherein the controller is configured to:
        control the temperature controller based on a predetermined recommended temperature of the delivery product such that the temperature inside the loading box sensed by the sensor corresponds to the recommended temperature; and drive the deodorizer when an odor sensed by the sensor is greater than or equal to a predetermined concentration, and wherein the controller is capable of controlling opening and closing of a cover of the loading box, and is further configured to:

open the cover for a predetermined time based on the sensing result of the sensor when the delivery product is loaded in the loading box; or open the cover for a predetermined time when a certain period of time passes after the delivery product loaded in the loading box is unloaded.

2. The delivery robot loading box state management system of claim 1, wherein the temperature controller comprises a cooling and heating device capable of performing functions of a heater and a cooler, or a liquid accommodated in a container capable of heating or cooling, which is loaded in the loading box.

3. The delivery robot loading box state management system of claim 1, wherein the deodorizer comprises a UV lamp.

4. The delivery robot loading box state management system of claim 1, wherein the delivery robot loading box state management system further comprises a fan capable of generating wind from the inside of the loading box to the outside, and the controller is configured to control the fan to be driven when the cover is opened.

5. The delivery robot loading box state management system of claim 1, wherein the controller is configured to control the temperature controller, when delivery of a first delivery product is completed, to correspond to a recommended temperature of a second delivery product to be delivered before the second delivery product is loaded.

6. The delivery robot loading box state management system of claim 1, wherein the controller is configured to drive the deodorizer before a second delivery product to be delivered is loaded when delivery of a first delivery product is completed.

\* \* \* \* \*